United States Patent [19]

Haisma et al.

[11] Patent Number: 5,757,883
[45] Date of Patent: May 26, 1998

[54] METHOD OF MANUFACTURING AN X-RAY OPTICAL ELEMENT FOR AN X-RAY ANALYSIS APPARATUS

[75] Inventors: Jan Haisma, Valkenswaard; Johannes F. M. D'Achard Van Enschut, Eindhoven; Cornelis L. Adema, Eindhoven; Jan C. Gijsbers, Eindhoven; Pieter K. De Bokx, Eindhoven, all of Netherlands

[73] Assignee: U.S. Philips Corporation, New York, N.Y.

[21] Appl. No.: 637,248

[22] Filed: Apr. 24, 1996

[30] Foreign Application Priority Data

Apr. 26, 1995 [FR] France .................. 95 201075

[51] Int. Cl.$^6$ .................................................. G21K 1/06
[52] U.S. Cl. ........................................ 378/84; 378/85
[58] Field of Search ................................ 378/84, 85

[56] References Cited

U.S. PATENT DOCUMENTS

| 3,439,163 | 4/1969 | de Jongh ..................... 378/84 |
| 4,788,703 | 11/1988 | Murakami et al. .............. 378/84 |
| 5,004,319 | 4/1991 | Smither ..................... 359/570 |

FOREIGN PATENT DOCUMENTS

| 0115892B1 | 8/1987 | European Pat. Off. ..... G01N 23/207 |
| 62-186204A | 8/1987 | Japan ..................... G02B 5/10 |
| 2105101 | 4/1990 | Japan . | |

OTHER PUBLICATIONS

Bertin, *Principles and Practice of X-ray Spectrometric Analysis*, Chapters 5.5 and 5.6, Plenum Press, New York-London, ISBN 0-306-20809-6), Second Edition, pp. 200-214, No Date.

Haisma et al, "Surface Preparation and Phenomenological Aspects of Direct Bonding", Philips Journal of Research, vol. 49, No. 1, (1995), pp. 1-24.

*Primary Examiner*—David P. Porta
*Assistant Examiner*—David Vernon Bruce
*Attorney, Agent, or Firm*—Anne E. Barschall

[57] ABSTRACT

A method of manufacturing an X-ray optical element. The element consists of a body of a material having a shape memory. At a high temperature, i.e. a temperature beyond the transition temperature of the material, the body is pressed so as to impart a first, desired shape. A surface of the body is thus shaped for example, as a logarithmic spiral or as another curved shape. After cooling to a low temperature, i.e. a temperature below the transition temperature of the material, a second, machinable shape is imparted to the body, preferably a flat surface. A number of precision operations can be performed on this second, machinable shape, for example polishing to a surface roughness of 0.5 nm RMS. Subsequent to this precision operation, the body is heated and resumes its first, desired shape which is retained after cooling. The body can be provided, if desired, with a comparatively thin surface layer which is also polished in the flat shape and which bends when the body resumes the desired shape. This layer can be chosen on the basis of desired mechanical (polishability) or X-ray optical properties. The X-ray optical element may comprise notably a multilayer mirror for X-ray purposes, thus forming a high-precision crystal for wavelength analysis.

10 Claims, 2 Drawing Sheets

METHOD OF MANUFACTURING AN X-RAY OPTICAL ELEMENT FOR AN X-RAY ANALYSIS APPARATUS

The invention relates to a method of manufacturing an X-ray optical element having a boundary surface in the form of a curved surface for interaction with X-rays incident thereon.

The invention also relates to an X-ray optical element manufactured by means of said method, and to an X-ray analysis apparatus comprising such an X-ray optical element.

Generally speaking. X-ray analysis apparatus require X-ray optical elements having a non-flat surface. Examples in this respect are analysis crystals having a cylindrical or spherical surface for the focusing of X-rays or logarithmically curved crystals which must satisfy the requirement that the entire crystal surface should participate in the so-called Bragg reflection when the crystal is exposed from a point-shaped or line-shaped X-ray source. For a further explanation of the various shapes of curved crystal surfaces reference is made to, for example the chapters 5.5 and 5.6 of "Principles and Practice of X-ray Spectrometric Analysis" (Second Edition), by Eugene P. Bertin, Plenum Press, New York-London (ISBN 0-306-30809-6).

A method of the kind set forth is known from European Patent Specification EP-0 115 892. The cited document describes a method of manufacturing an X-ray optical element in the form of an assembly of a support on which an X-ray analysis crystal is mounted for use in an X-ray analysis apparatus. The crystal has a boundary surface on which the X-rays to be analyzed are incident and which is curved so as to have a spherical shape for focusing the X-rays to be analyzed. The desired boundary surface shape is obtained by grinding one of the flat surfaces of a plano-parallel crystal plate so that is has a spherical shape with a first radius of curvature, the crystal plate thus ground subsequently being pressed in a mould. The mould has a spherical surface with a second radius of curvature against which the crystal plate with the remaining flat surface is pressed, after which it is glued thereto. Because of the combination of the two radii of curvature, a crystal surface having the desired properties as regards focusing and radiation acceptance angle is realized. An X-ray optical element in the form of an assembly of a mould (the support) and an analysis crystal is thus obtained.

It is a drawback of the known method that after the manufacture of the X-ray optical element, the mould is no longer available for further production. This is a particularly serious drawback in the case of moulds having a complex shape and/or a high shape stability, because such moulds are expensive. It is another drawback that this method of manufacturing can be used for a limited number of shapes only (notably spherical or cylindrical shapes).

It is an object of the invention to provide a method of manufacturing an X-ray optical element whose surface approximates the desired shape with high precision, and is sufficiently smooth, its smoothness being of light optical or even X-ray optical quality in given circumstances.

To this end, the method of the invention is characterized in that it comprises a combination of the following steps: forming a body for the X-ray optical element from a material having a shape memory with a given transition temperature, said formation comprising: imparting a first, desired shape to the body at a temperature beyond the transition temperature; imparting a second, machinable shape to the body at a temperature below the transition temperature; carrying out a superfinishing operation in the form of a grinding or polishing operation on the machinable shape, said operation being applied to a surface of the support thus formed; returning the body to the first, desired shape after completion of the polishing or grinding operation, by heating it to a temperature beyond the transition temperature.

The invention is based on the idea that both requirements (i.e. proper shape and required surface smoothness) can be separately satisfied. The body of a material having a shape memory can be given approximately the first, desired shape by pressing it in a mould at a high temperature (beyond the transition temperature). The temperature at which the body is pressed so as to assume the first shape can be chosen to be so high that the material to be pressed exhibits only plastic deformation and no longer elastic deformation; the workpiece can thus adopt the shape of the mould with a high precision.

Conventional means can be used to impart approximately the correct shape to the mould. This can be realised, for example by means of a numerically controlled milling machine. Thus, a mould is obtained which approximates the desired shape because it is composed of a large number of, for example plane surfaces. When the body formed in such a mould is cooled to ambient temperature (below the transition temperature), the second, machinable shape can be imparted thereto by pressing it in another mould. This shape is chosen so that the superfinishing of the surface can be suitably carried out.

Preferably, said second shape is a plane surface or a spherical surface. Notably a plane surface can be superfinished to a very high degree of smoothness (up to a roughness of the order of magnitude of 0.5 nm RMS, where RMS is the Root Mean Square value). If the superfinished support is heated beyond the transition temperature again, it assumes the desired shape again, but with a much smoother surface. Even though the surface of the shape memory material is roughened to a given extent during the return to the desired shape, such roughening will be so slight that it is insignificant for many applications.

It is to be noted that from Japanese Patent 62-186204 it is known to manufacture a concave mirror from a material having a shape memory. The focal distance of the mirror can be changed by varying the temperature of the mirror body. However, the idea of imparting the desired shape at the high temperature, followed by choosing a shape suitable for accurate surface finishing at the low temperature, cannot be extracted from the cited document.

The body thus obtained, having the desired, smooth surface, can be used directly for interaction with incident X-rays. However, it may occur that the shape memory material does not have the desired X-ray optical properties or that said slight roughening of the surface by the return to the first, desired shape is still objectionable for the relevant application of the X-ray optical element. In accordance with a further embodiment of the invention, the body in the second, machinable shape can then be provided, on its superfinished surface, with a comparatively thin surface layer for interaction with the X-rays. Said residual roughness is so slight that it has no effect on the smoothness of the surface of the comparatively thin surface layer exposed to the X-rays. The thickness of this layer is such that it readily bends together with the support but the (slight) remaining roughness of the curved surface of the body cannot be observed in the free surface of the surface layer.

The material of the comparatively thin surface layer can be selected, if desired, so as to consist of a material which can be suitably superfinished. In an embodiment of the invention, the comparatively thin surface layer on the body in the second, machinable shape can then be subjected to superfinishing in the form of a grinding or polishing operation. Any slight irregularities still present in the surface layer are removed by this final polishing treatment, resulting in an extremely smooth surface which remains smooth when the surface is deformed at a later stage.

The material of the surface layer can also be selected on the basis of X-ray optical properties, for example as desired for total X-ray reflection. In that case the surface layer may consist of gold for which a critical angle for total reflection of approximately ten mrad exists in the case of an X-ray wavelength of 0.13 nm (this value is approximately 0.4 times larger for the same wavelength in the case of silicon). Another advantage of gold consists in that this material exhibits practically no corrosion, so that it constitutes a very stable surface layer.

Preferably, the surface layer in a further embodiment of the invention consists of silicon. The properties of this material are very well known from the manufacture of semiconductors and this material is also readily available commercially. It has been found that it can be suitably polished and that layers of this material can be suitably machined down to a very small thickness (less than 10 µm) when provided on a suitable substrate acting as the supporting element.

In a further embodiment of the invention, a multilayer mirror for X-ray purposes is provided on the comparatively thin surface layer. When the comparatively thin surface layer is chosen to be such (for example, of silicon) that it can be very accurately polished, the surface layer can be used as a substrate for a multilayer mirror. Such mirrors consist of alternating layers of different materials whose period is typically of the order of magnitude of comparatively longwave X-rays, for example 3–10 nm. For such a layer thickness, of course, the substrate should have a roughness which is substantially smaller, for example of the order of magnitude of 0.5 nm. This small roughness can be achieved by means of a polishing operation executed on the second, machinable shape; the multilayer mirror can subsequently be used for X-ray optical purposes in the first, desired shape.

These and other aspects of the invention will be apparent from and elucidated with reference to the embodiments described hereinafter.

In the drawings:

FIGS. 1a and 1b show respective examples of a configuration in which an X-ray optical element having a curved surface can be used for interaction with X-rays.

Figure 1A:
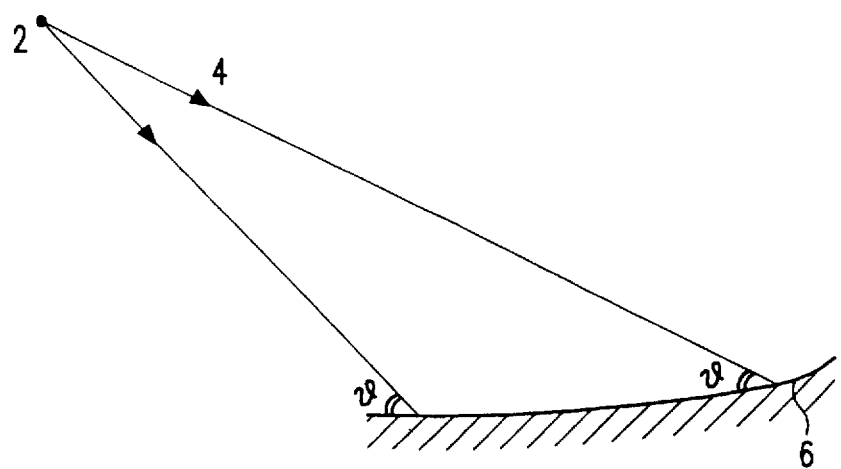
FIG. 1a illustrates the use of an X-ray optical element for wavelength analysis of X-rays.

FIG. 1a shows diagrammatically a source 2 emitting X-rays 4 which are reflected by diffraction by an analysis crystal 6. Crystals of this kind are used in X-ray analysis apparatus for wavelength analysis of X-rays from the specimen to be examined.

Wavelength analysis is based on the known Bragg relation: $2 \cdot d \cdot \sin v = n\lambda$, in which d is the distance between the crystal faces in the crystal on which X-ray reflection occurs, v=the angle at which the X-rays are incident on the crystal faces, λ is the wavelength of the X-rays, and n is the order of the reflection. In analysis equipment the X-rays to be analyzed often originate from a source of X-rays of small dimensions, for example a specimen to be examined, in which X-rays to be analyzed are excited by primary radiation. For example, the dimensions of such a source area are of the order of magnitude of 2 cm, whereas the distance between the source area and the detector is of the order of magnitude of 30 cm. A problem is then encountered in that in the case of a flat analysis crystal, the radiation emanating from the point-shaped source is not incident at the same angle v at all points on the crystal. Said Bragg relation will be satisfied only in an area having (approximately) the shape of a narrow rectangle on the crystal. This means that only a small part of the crystal surface is used for wavelength analysis of the incident X-rays; the radiation incident outside said line-shaped area is not involved in the detection, thus causing longer measuring periods or a poor signal-to-noise ratio of the signal to be detected. It is known to solve this problem by bending the crystal so as to have the shape of a logarithmic spiral. In the case of such a crystal the entire surface participates in the Bragg reflection, so that said problem does not arise.

It appears from the above Bragg relation that for longwave X-rays (λ greater than, for example 1 nm) the distance d between the crystal faces in the analysis crystal no longer suffices to enable Bragg reflection. In that case multilayer X-ray mirrors (also referred to as "synthetic crystals") which have a period of, for example 3–10 nm are sometimes used. In accordance with the method of the invention, the curved surface (during use) of the analysis crystal 6 can be smoothed to such an extent that this surface can serve as a substrate for the multilayer mirror. If desirable, a suitable intermediate layer can be provided between the surface of the crystal 6 and the multilayer mirror. Silicon can be used for this purpose, because this material can be very readily polished to the (very small) surface roughness then required.

Figure 1B:
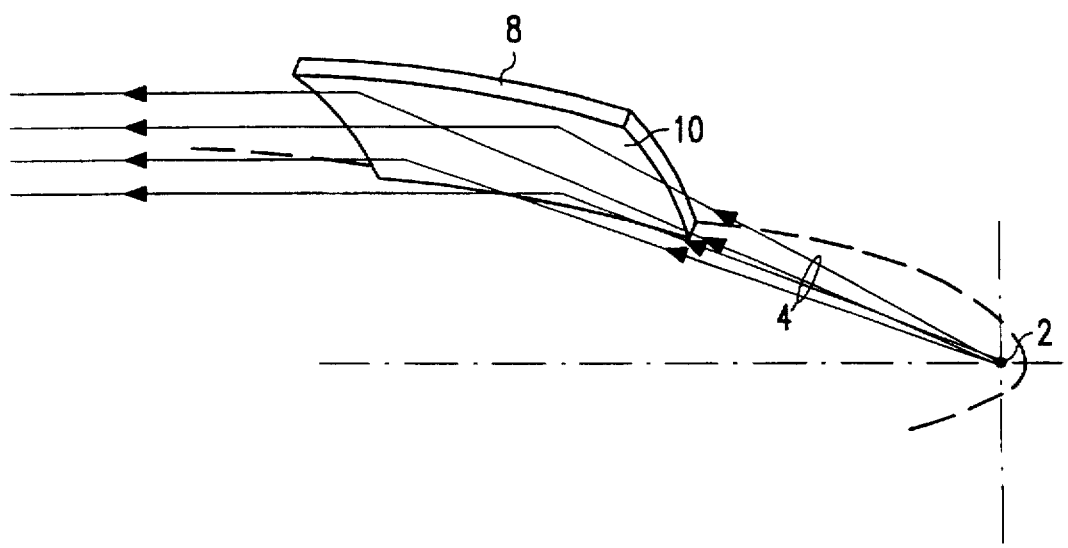
FIG. 1b illustrates the use of an X-ray optical element so as to obtain a parallel beam of X-rays by way of total reflection.

FIG. 1b again shows diagrammatically a source 2 emitting X-rays 4 which are incident at a grazing angle on an X-ray optical element 8 having a curved surface. In this case it is assumed that the X-ray optical element 8 constitutes a reflector for total reflection of X-rays; this is achieved by making the radiation 4 incident on the curved surface 10 at such an angle that across the entire surface 10 the angle of incidence (i.e. the angle between the surface and the incident beam) is smaller than the critical angle for total reflection of X-rays. The value of this critical angle is dependent on the wavelength of the X-rays to be reflected and on the material of the surface 10, but is of the order of magnitude of 10 mrad for the customary values. It is assumed that for experimental purposes a parallel beam of X-rays is to be obtained with a comparatively high intensity. This can be achieved by choosing the reflection surface 10 in the form of (a part of) a paraboloid of revolution which, as is known, has the property of reflecting radiation emanating from one point (the focal point) as a parallel beam. In the case of an (approximately) linear source, of course, a surface in the form of a cylindrical parabola can be chosen.

In order to enable the small critical angles for total reflection to be achieved, the surface 10 of the paraboloid should have such a surface roughness, i.e. be so smooth, that these grazing angles are feasible. This is because when it is attempted to make X-rays incident on a rough surface at a very small angle, in most locations the X-rays will not strike the matter at the desired small angle, but at an arbitrary angle which is dependent only on the position of the local surface element on which the radiation is incident. For this situation the invention can thus also offer a sufficiently smooth surface, if desired, a comparatively thin surface layer having the desired X-ray optical properties can be provided on the surface.

FIGS. 2a to 2d diagrammatically illustrate a number of steps for carrying out the method of the invention.

Figure 2A:
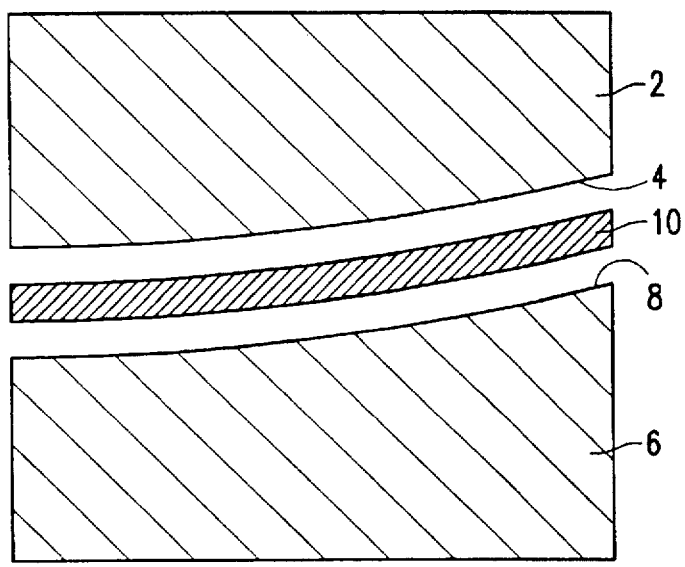
FIGS. 2a to 2d are diagrammatic views of the X-ray optical element in various stages of manufacture.

In FIG. 2a a plate 10 of a material having a shape memory is pressed between two moulds 2 and 6 of the desired shape at a temperature beyond the transition temperature in order to impart the desired shape to the plate. The surfaces 4 and 8 of the moulds may in principle have any desired shape, for example a cylinder having a cross-section in the form of a logarithmic spiral perpendicularly to the cylinder axis, or as a part of a paraboloid of revolution, as may be desirable for X-ray analysis equipment.

The shape of the surfaces can be imparted by means of any known manufacturing technique, for example milling by means of a numerically controlled milling machine. Any desired shape can thus be suitably approximated, be it that this process leaves traces behind in the form of small plane faces or line tracks of the tool. Consequently, the surfaces thus machined, including the surfaces of the workpiece, do not have the low surface roughness required for X-ray analysis. This roughness is reduced by the superfinishing of the workpiece to be described hereinafter.

The shape memory material is, for example TiNi having a transition temperature of 68° C. This material is heated to 475° C., at which temperature the plate 10 is pressed into a first, desired shape. Because of the comparatively high temperature at which this operation takes place, no disturbing elastic deformation of the material occurs so that the workpiece retains this first shape after cooling. The workpiece is cooled to a temperature below the transition temperature of 68° C., for example to an ambient temperature of 20° C. At that temperature the workpiece still has the first, desired shape.

Figure 2B:
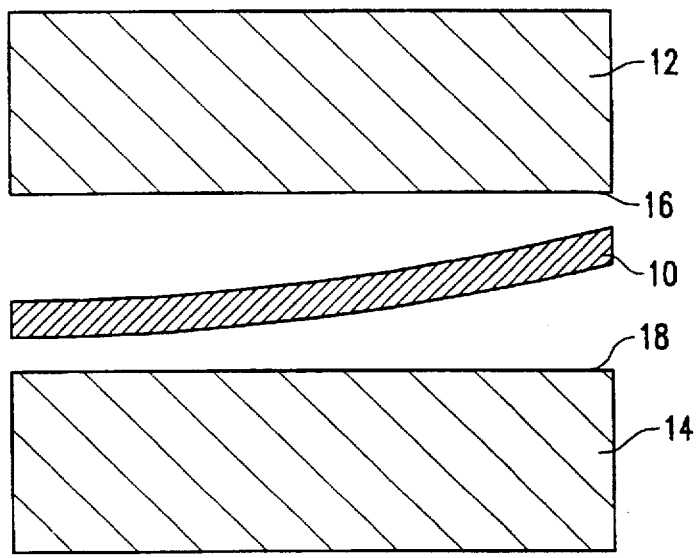

FIG. 2b shows that the workpiece 10 thus obtained is clamped between two other moulds 12 and 14 in order to impart the second, machinable shape to the plate. The surfaces 16 and 18 of these moulds can in principle have any shape enabling suitable superfinishing of the workpiece in the form of a grinding or polishing operation. In dependence on the requirements imposed as regards the surface roughness of the workpiece, this shape may be, for example spherical, cylindrical or flat. In order to satisfy the very severe requirements as regards surface roughness, preferably a flat surface is chosen. At said ambient temperature the workpiece is pressed between the two moulds 12 and 14, having the flat surfaces 16 and 18, respectively, so that the workpiece adapts the second, machinable shape.

In this second, machinable shape (the flat shape) the superfinishing in the form of a grinding or polishing operation can be carried out on the surface of the body thus formed. The surface roughness to be achieved is dependent on the relevant application. If the body of shape memory material itself is to interact with the X-rays, an appropriate surface roughness must be chosen; this roughness can always be achieved by polishing. When the body of shape memory material is to serve as a support for further X-ray optical materials, the surface roughness may vary between somewhat broader limits. A first possibility consists in that the body is intended to serve as a support for a surface layer (not a multilayer mirror) which is capable of following the bending of the surface of the body but has a thickness such that the roughness of the body surface cannot be observed on the free surface of this surface layer. In that case less severe requirements are imposed as regards the surface roughness of the shape memory material. A second possibility consists in that a multilayer mirror for X-rays is provided directly on the shape memory material. In that case the surface roughness of the superfinished surface must be of the order of magnitude of 0.5 nm. A third possibility consists in that the multilayer mirror is provided on a suitable surface layer of, for example silicon. Evidently, in that case the surface of the silicon must satisfy the severe roughness requirements.

Figure 2C:
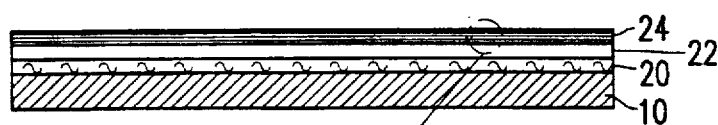
Figure 2D:
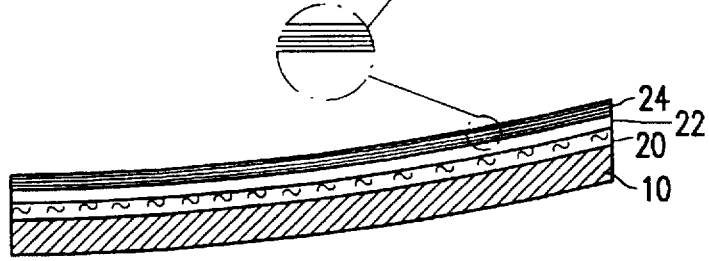

It is assumed that a surface layer of silicon of a thickness of 10 μm is to be provided on the body of shape memory material and that a multilayer mirror is to be provided on this surface layer. In that case the curved surface of the body is first polished until its roughness can no longer be observed in the surface of the silicon layer, for example to a roughness of a few micrometers. Subsequently, the surface layer of a thickness of 125 μm is bonded to the (still flat) surface of the body by means of a cold-hardening two-component glue, for example an epoxy resin with a hardener. After the glue has hardened, the silicon layer can be polished in known manner, for example as described in an article in "Philips Journal of Research", Vol. 49, No. 1 (1995), entitled "Surface preparation and phenomenological aspects of direct bonding". This article describes, notably in its sections 3.5 and 3.6, a method of polishing a silicon surface whereby a surface roughness of 0.5 nm is achieved. After the polishing of the silicon surface, the further layers of the multilayer mirror can be provided a manner which is known per se. FIG. 2c shows the result in the form of a flat X-ray optical element consisting of the body 10 on which a comparatively thin silicon surface layer 22 has been bonded by way of a layer of glue 20. On the silicon layer 22 there is provided the multilayer mirror 24. After such formation of a flat X-ray optical element, it is heated to a temperature beyond the transition temperature of 68° C.; the element then assumes the desired prebent shape as shown in FIG. 2d. After cooling to ambient temperature, the element retains its shape and is ready for use in an X-ray analysis apparatus.

We claim:

1. A method of manufacturing an X-ray optical element having a boundary surface in the form of a curved surface for interaction with X-rays incident thereon, characterized in that the method comprises the following steps:

forming a body for the X-ray optical element from a material having a shape memory with a given transition temperature, said formation comprising:
imparting a first, desired shape to the body at a temperature beyond the transition temperature,
imparting a second, machinable shape to the body at a temperature below the transition temperature,
carrying out a superfinishing operation in the form of a grinding or polishing operation on the machinable shape, said operation being applied to a surface of the support thus formed;
returning the body to the first, desired shape, after completion of the polishing or grinding operation, by heating it to a temperature beyond the transition temperature.

2. A method as claimed in claim 1, characterized in that the body surface to be superfinished in the second, machinable shape is a flat surface or a spherical surface.

3. A method as claimed in claim 1, in which on the superfinished surface of the body in the second, machinable shape there is provided a comparatively thin surface layer for interaction with the X-rays.

4. A method as claimed in claim 3, in which a superfinishing operation in the form of a grinding or polishing operation is carried out on the comparatively thin surface layer on the body in the second, machinable shape.

5. A method as claimed in claim 3, in which the comparatively thin surface layer consists of silicon.

6. A method as claimed in claim 3, in which a multilayer mirror for X-ray purposes is provided on the comparatively thin surface layer.

7. An X-ray analysis apparatus comprising an X-ray optical element having a surface for interaction with X-rays, characterized in that said element comprises a body consisting of a material having a shape memory.

8. An X-ray analysis apparatus as claimed in claim 7, characterized in that a comparatively thin surface layer for interaction with the X-rays is provided on the body.

9. An X-ray analysis apparatus as claimed in claim 8, characterized in that a multilayer mirror for X-ray purposes is provided on the comparatively thin surface layer.

10. An X-ray optical element for use in an X-ray analysis apparatus as defined in claims 7.

* * * * *